United States Patent
Dreyfus et al.

(10) Patent No.: US 11,214,576 B2
(45) Date of Patent: Jan. 4, 2022

(54) 2,3-DIHYDROFURO[2,3-B]PYRIDINE COMPOUNDS

(71) Applicant: Eli Lilly and Company, Indianapolis, IN (US)

(72) Inventors: Nicolas Jacques Francois Dreyfus, Surrey (GB); Andrew Faller, Surrey (GB)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 17/053,194

(22) PCT Filed: Jun. 14, 2019

(86) PCT No.: PCT/US2019/037232
§ 371 (c)(1),
(2) Date: Nov. 5, 2020

(87) PCT Pub. No.: WO2019/245907
PCT Pub. Date: Dec. 26, 2019

(65) Prior Publication Data
US 2021/0070766 A1 Mar. 11, 2021

Related U.S. Application Data

(60) Provisional application No. 62/688,434, filed on Jun. 22, 2018.

(51) Int. Cl.
C07D 491/048 (2006.01)
(52) U.S. Cl.
CPC .................. *C07D 491/048* (2013.01)
(58) Field of Classification Search
CPC .................................. C07D 491/048
See application file for complete search history.

(56) References Cited

U.S. PATENT DOCUMENTS

| | | |
|---|---|---|
| 4,921,887 A | 5/1990 | Matsui et al. |
| 9,120,781 B2 | 9/2015 | Li et al. |
| 10,081,625 B2 | 9/2018 | Dreyfus et al. |
| 10,377,750 B2 | 8/2019 | Dreyfus et al. |
| 2016/0031871 A1 | 2/2016 | Yu et al. |

FOREIGN PATENT DOCUMENTS

| | | |
|---|---|---|
| WO | 2005/014579 A1 | 2/2005 |
| WO | 2014/159234 A1 | 10/2014 |
| WO | 2016/030443 A1 | 3/2016 |
| WO | 2017/106254 A1 | 6/2017 |
| WO | 2017/144633 A1 | 8/2017 |
| WO | 2017/144639 A1 | 8/2017 |

OTHER PUBLICATIONS

Boström, et al., "Oxadizaoles in Medicinal Chemistry," J. Med. Chem 2012, 55, 1817-1830.
Somani, et al., "Oxadiazole: A biologically important heterocycle," Der Pharma Chemica: 2009, 1(1):130-140.

*Primary Examiner* — Rebecca L Anderson
(74) *Attorney, Agent, or Firm* — Nelsen L. Lentz

(57) ABSTRACT

The present invention provides a compound of Formula I: wherein R is H or F; or a pharmaceutically acceptable salt thereof, and the use of compounds of Formula I for treatment of neurodegenerative diseases, such as Alzheimer's disease.

Formula I

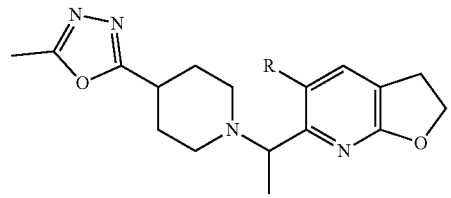

14 Claims, No Drawings

2,3-DIHYDROFURO[2,3-B]PYRIDINE COMPOUNDS

The present invention relates to novel 2,3-dihydrofuro[2,3-b]pyridine compounds, to pharmaceutical compositions comprising the compounds, to methods of using the compounds to treat neurodegenerative disorders such as Alzheimer's disease (AD), and to intermediates and processes useful in the synthesis of the compounds.

The present invention is in the field of treatment of AD, progressive supranuclear palsy (PSP) and other diseases and disorders involving tau-mediated neurodegeneration, known collectively as tauopathies.

AD is a devastating neurodegenerative disorder that affects millions of patients worldwide. In view of the currently approved agents on the market which afford only transient symptomatic benefits to the patient, there is a significant unmet need in the treatment of AD.

The oligomerization of the microtubule-associated protein tau into filamentous structures such as paired helical filaments (PHFs) and straight or twisted filaments, which give rise to neurofibrillary tangles (NFTs) and neuropil threads (NTs), is one of the defining pathological features of AD and other tauopathies. The number of NFTs in the brains of individuals with AD has been found to correlate closely with the severity of the disease, suggesting tau has a key role in neuronal dysfunction and neurodegeneration (Nelson et al., *J Neuropathol Exp Neurol.*, 71(5), 362-381(2012)). Tau pathology has been shown to correlate with disease duration in PSP in that cases with a more aggressive disease course have a higher tau burden than cases with a slower progression. (Williams et al., *Brain*, 130, 1566-76 (2007)).

Past studies (Yuzwa et al., *Nat Chem Biol*, 4(8), 483-490 (2008)) support the therapeutic potential of O-GLNAcase (OGA) inhibitors to limit tau hyperphosphorylation, and aggregation into pathological tau, for the treatment of AD and related tau-mediated neurodegeneration disorders. More recently, the OGA inhibitor Thiamet-G has been linked to slowing motor neuron loss in the JNPL3 tau mouse model (Yuzwa et al., *Nat Chem Biol*, 8, 393-399 (2012)), and to a reduction in tau pathology and dystrophic neurites in the Tg4510 tau mouse model (Graham et al., *Neuropharmacology*, 79, 307-313 (2014)). Accordingly, OGA inhibitors are recognized as a viable therapeutic approach to reduce the accumulation of hyperphosphorylated, pathological forms of tau.

WO 2016/030443 A1 discloses certain glycosidase inhibitors useful in the treatment of tauopathies. WO 2017/144639 A1 and WO 2017/144633 A1 disclose certain glycosidase inhibitors useful in the treatment of tauopathies and AD.

OGA inhibitors that are brain penetrant are desired to provide treatments for tau-mediated neurodegeneration disorders, such as Alzheimer's disease and PSP. The present invention provides certain novel compounds that are potent inhibitors of OGA. In addition, the present invention provides certain novel compounds that are potent inhibitors of OGA with the potential to be sufficiently brain penetrant to effectively treat tauopathies, such as AD and PSP.

Accordingly, the present invention provides a compound of Formula I

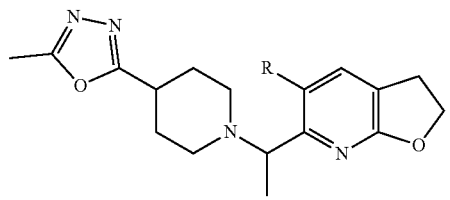

Formula I wherein R is H or F, or a pharmaceutically acceptable salt thereof.

The present invention also provides a method of treating Alzheimer's disease in a patient in need of such treatment, comprising administering to the patient an effective amount of a compound of Formula I, or a pharmaceutically acceptable salt thereof.

The present invention further provides a method of treating the progression of mild cognitive impairment to Alzheimer's disease in a patient in need of such treatment, comprising administering to the patient an effective amount of a compound of Formula I, or a pharmaceutically acceptable salt thereof.

The present invention also provides a method of treating progressive supranuclear palsy in a patient in need of such treatment, comprising administering to the patient an effective amount of a compound of Formula I, or a pharmaceutically acceptable salt thereof. The present invention also provides a method of treating tau-mediated neurodegenerative disorders in a patient, comprising administering to a patient in need of such treatment an effective amount of a compound of Formula I, or a pharmaceutically acceptable salt thereof.

Furthermore, this invention provides a compound of Formula I, or a pharmaceutically acceptable salt thereof for use in therapy, in particular for use in treating Alzheimer's disease or for use in preventing the progression of mild cognitive impairment to Alzheimer's disease. In addition, this invention provides a compound of Formula I, or a pharmaceutically acceptable salt thereof for use in treating progressive supranuclear palsy. The invention also provides a compound of Formula I, or a pharmaceutically acceptable salt thereof for use in treating tau-mediated neurodegenerative disorders.

Even furthermore, this invention provides the use of a compound of Formula I, or a pharmaceutically acceptable salt thereof, for the manufacture of a medicament for treating Alzheimer's disease or for preventing the progression of mild cognitive impairment to Alzheimer's disease. In addition, this invention provides the use of a compound of Formula I, or a pharmaceutically acceptable salt thereof, for the manufacture of a medicament for treating progressive supranuclear palsy. The invention also provides the use of a compound of Formula I, or a pharmaceutically acceptable salt thereof, for the manufacture of a medicament for treating tau-mediated neurodegenerative disorders.

The invention further provides a pharmaceutical composition, comprising a compound of Formula I, or a pharmaceutically acceptable salt thereof, with one or more pharmaceutically acceptable carriers, diluents, or excipients. The invention further provides a process for preparing a pharmaceutical composition, comprising admixing a compound of Formula I, or a pharmaceutically acceptable salt thereof, with one or more pharmaceutically acceptable carriers, diluents, or excipients.

Mild cognitive impairment has been defined as a potential prodromal phase of dementia associated with Alzheimer's disease based on clinical presentation and on progression of patients exhibiting mild cognitive impairment to Alzheimer's disease over time. The term "preventing the progression of mild cognitive impairment to Alzheimer's disease" includes restraining, slowing, stopping, or reversing the progression of mild cognitive impairment to Alzheimer's disease in a patient.

As used herein, the terms "treating" or "to treat" includes restraining, slowing, stopping, or reversing the progression or severity of an existing symptom or disorder.

As used herein, the term "patient" refers to a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be determined by one skilled in the art by the use of known techniques and by observing results obtained under analogous circumstances. In determining the effective amount for a patient, a number of factors are considered, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances. The compounds of the present invention are effective at a dosage per day that falls within the range of about 0.1 to about 15 mg/kg of body weight.

The compounds of the present invention are formulated as pharmaceutical compositions administered by any route which makes the compound bioavailable. Preferably, such compositions are for oral administration. Such pharmaceutical compositions and processes for preparing same are well known in the art (See, e.g., Remington: The Science and Practice of Pharmacy, L. V. Allen, Editor, 22$^{nd}$ Edition, Pharmaceutical Press, 2012).

The compounds of Formula I and the pharmaceutically acceptable salts thereof are particularly useful in the treatment methods of the invention, with certain configurations being preferred. The following list of compounds of the present invention describe such configurations. It will be understood that these preferences are applicable both to the treatment methods and to the compounds of the invention.

Compounds of the present invention include:

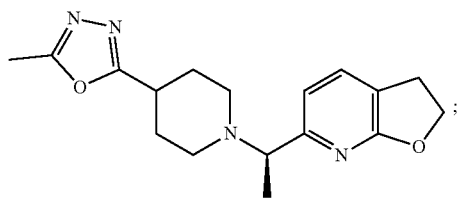

Formula Ia(i)

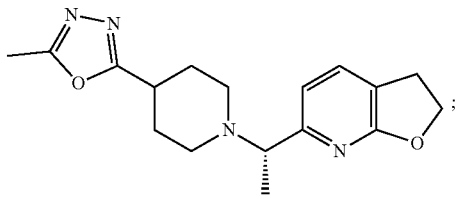

Formula Ia(ii)

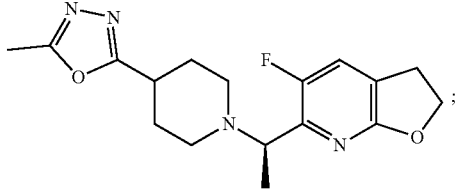

Formula Ib(i)

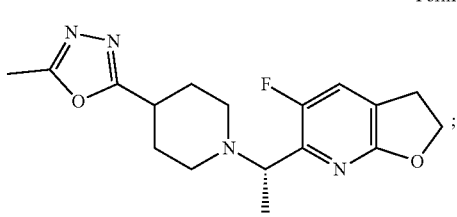

Formula Ib(ii)

(−)-6-[1-[4-(5-methyl-1,3,4-oxadiazol-2-yl)-1-piperidyl]ethyl]-2,3-dihydrofuro[2,3-b]pyridine;
(+)-6-[1-[4-(5-methyl-1,3,4-oxadiazol-2-yl)-1-piperidyl]ethyl]-2,3-dihydrofuro[2,3-b]pyridine;
(−)-5-fluoro-6-[1-[4-(5-methyl-1,3,4-oxadiazol-2-yl)-1-piperidyl]ethyl]-2,3-dihydrofuro[2,3-b]pyridine; and
(+)-5-fluoro-6-[1-[4-(5-methyl-1,3,4-oxadiazol-2-yl)-1-piperidyl]ethyl]-2,3-dihydrofuro[2,3-b]pyridine;
and pharmaceutically acceptable salts thereof.

Individual enantiomers may be separated or resolved by one of ordinary skill in the art at any convenient point in the synthesis of compounds of the invention, by methods such as selective crystallization techniques, chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994), or supercritical fluid chromatography (SFC) (See for example, T. A. Berger; "*Supercritical Fluid Chromatography Primer*," Agilent Technologies, July 2015).

As used herein, the methyl group at chiral position 1 as drawn below with a wavy bond:

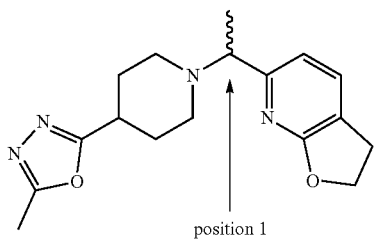 [SMILES: Cc1nnc(C2CCN(C(C)c3ccc4c(n3)OCC4)CC2)o1]

position 1 indicates that the compound is a single enantiomer; however, the absolute configuration, (R) or (S), at this chiral center on the compound has not been determined and the compound corresponds to either the (−) or (+) enantiomer as indicated in the name for each of the relevant Preparations and Examples below. It is further understood by one of ordinary skill in the art that the (−) or (+) designation is an empirical value indicating the direction of optical rotation exhibited by the particular enantiomer which may vary depending upon certain variables, such as temperature, solvent used, concentration, and wavelength of light used when measuring the optical rotation.

A pharmaceutically acceptable salt of the compounds of the invention can be formed, for example, by reaction of an appropriate free base of a compound of the invention and an appropriate pharmaceutically acceptable acid in a suitable solvent under standard conditions well known in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

The compounds of the present invention, or salts thereof, may be prepared by a variety of procedures known to one of ordinary skill in the art, some of which are illustrated in the schemes, preparations, and examples below. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Without limiting the scope of the invention, the following schemes, preparations, and examples are provided to further illustrate the invention. In addition, one of ordinary skill in the art appreciates that compounds of Formula I may be prepared by using starting material or intermediate with the corresponding desired stereochemical configuration which can be prepared by one of skill in the art.

Certain abbreviations are defined as follows: "ACN" refers to acetonitrile; "Ac" refers to acetyl; "AcOH" refers to acetic acid; "Ac₂O" refers to acetic anhydride; "dba" refers to dibenzylideneacetone; "DCM" refers to methylene chloride or dichloromethane; "DIPEA" refers to diisopropylethylamine; "DMEA" refers to dimethylethylamine; "DMSO" refers to dimethyl sulfoxide; "dppf" refers to diphenylphoshinoferrocene; "EDTA" refers to ethylenediaminetetraacetic acid; "ES/MS" refers to Electrospray Mass Spectrometry; "EtOAc" refers to ethyl acetate; "EtOH" refers to ethanol or ethyl alcohol; "h" refers to hour or hours; "IPA" refers to isopropanol or isopropyl alcohol; "IPAm" refers to isopropyl amine; "LiHMDS" refers to lithium bis(trimethylsilyl)amide; "KOtBu" refers to potassium-tert-butoxide; "Me" refers to methyl; "MTBE" refers to methyl-tert-butyl ether; "min" refers to minute or minutes; "n-BuLi" refers to n-butyllithium; "OAc" refers to acetate; "RT" refers to room temperature; "SFC" refers to Supercritical Fluid Chromatography; "TEA" refers to triethylamine; "THF" refers to tetrahydrofuran; "TMA" refers to trimethylamine; "TMEDA" refers to tetramethylethylenediamine; "Tris" refers to tris(hydroxymethyl)aminomethane or 2-amino-2-(hydroxymethyl)propane-1,3-diol; "[α]$_D^{20}$" refers to specific optical rotation at ° C. and 589 nm, wherein c is the concentration in g/100 mL.

Scheme 1

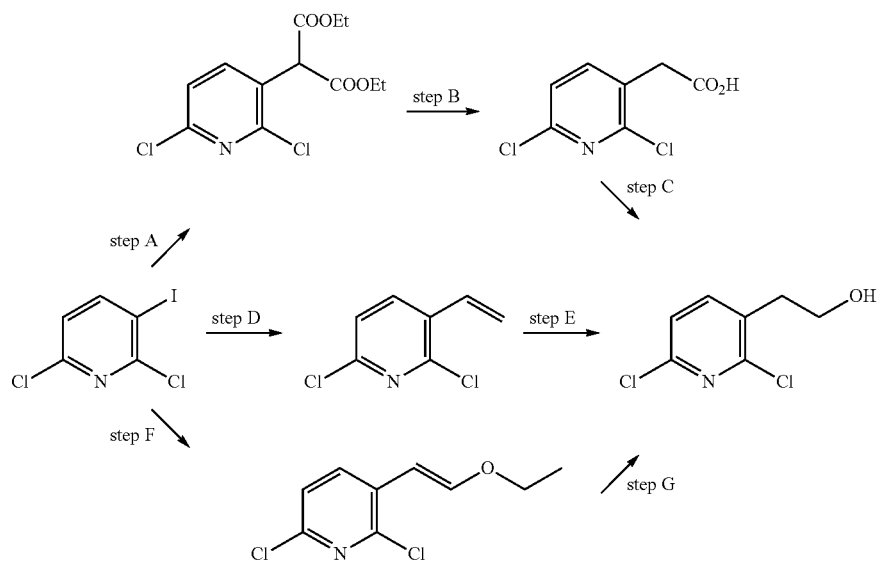

Scheme 1 depicts several syntheses of 2-(2,6-dichloro-3-pyridyl)ethanol from 2,6-dichloro-3-iodopyridine. In step A, a cross-coupling arylation of diethyl malonate via transition-metal catalysis may be accomplished, as is well known in the art. For example, about 1 equivalent of 2,6-dichloro-3-iodopyridine may be heated to about 80° C. with about 1.5 to 2.5 equivalents of diethyl malonate and about 3 equivalents of a suitable base, such as Cs₂CO₃, in a suitable polar organic solvent, such as 1,4-dioxane, in the presence of about 0.05-0.06 equivalents of CuI and 0.1-0.15 equivalents of picolinic acid for about 4-8 h. The resulting reaction product may be isolated by techniques well known in the art, such as extraction methods. For example, the cooled reaction mixture may be diluted with an appropriate aqueous salt solution, such as NH₄Cl, and extracted with an appropriate organic solvent, such as DCM, Et₂O, or EtOAc. The combined organic extracts may be washed with saturated aqueous NaCl, dried over MgSO$_4$, filtered, and the filtrate concentrate under reduced pressure, to obtain diethyl 2-(2,6-dichloro-3-pyridyl)propanedioate, the product of Scheme 1, step A, sufficient for additional use without additional purification.

In scheme 1, step B, hydrolytic thermal decarboxylation is well described in the art. For example, about 1 equivalent of diethyl 2-(2,6-dichloro-3-pyridyl)propanedioate, the product of Scheme 1, step A, may be heated at reflux in an aqueous mineral acid, such as HCl. The resulting reaction product may be isolated by techniques well known in the art, such as filtration. For example, the resulting precipitate observed in the cooled decarboxylative reaction mixture may be collected by filtration to obtain 2-(2,6-dichloro-3-pyridyl)acetic acid, the product of Scheme 1, step B, sufficient for additional use without additional purification.

Reduction of the acid moiety of 2-arylacetic acid in Scheme 1, step C, is well known in the art and may be accomplished under a wide array of reducing conditions. For example, about 1 equivalent of 2-(2,6-dichloro-3-pyridyl)acetic acid, the product of Scheme 1, step B, may be dissolved in a polar organic solvent, such as THF or 1,4-dioxane, and treated with a suitable reducing agent, such as 1.2-2.2 equivalents of borane-THF complex at about 0° C. The resulting reaction product may be isolated by techniques well known in the art, such as evaporation. For example, the borane-reaction mixture may be quenched with a suitable polar protic solvent, such as MeOH, and the resulting reaction mixture may be concentrated under reduced pressure to obtain the crude 2-(2,6-dichloro-3-pyridyl)ethanol, the product of Scheme 1 step C, sufficient for additional use without additional purification.

Alternatively, 2-(2,6-dichloro-3-pyridyl)ethanol may be prepared from 2,6-dichloro-3-iodopyridine via a Suzuki cross-coupling reaction, to obtain a 3-vinyl-pyridine intermediate, and a subsequent hydroboration. For example, in Scheme 1, step D, about 1 equivalent of 2,6-dichloro-3-iodopyridine may be heated under argon or nitrogen at about 90° C. for 18-36 h in a suitable polar organic solvent, such as EtOH, DMF, DMSO, or 1,4-dioxane, containing about 1-1.1 equivalents of potassium vinyltrifluoroborate, about 0.1-0.2 equivalents of a suitable transition metal-ligand catalyst, such as [1,1'-bis(diphenylphosphino)ferrocene] dichloropalladium, tetrakis(triphenylphosphine) palladium or bis(triphenylphosphine)palladium(II) dichloride, and about 0.2-0.3 equivalents of a suitable base, such as K$_2$CO$_3$, Cs$_2$CO$_3$, Na$_2$CO$_3$, or K$_3$PO$_4$. The resulting reaction product may be isolated by techniques well known in the art, such as extraction and column chromatography. For example, the reaction mixture may be diluted with a suitable organic solvent, such as EtOAc or DCM, the phases may be separated, the organic extract may be washed with saturated aqueous NaCl, dried over MgSO$_4$, filtered, filtered, and the filtrate may be concentrated under reduced pressure. The resulting residue may be subjected to flash chromatography over silica gel, eluting with a suitable organic solvent mixture, such as about 1:0 to about 0:1 cyclohexane and EtOAc, to obtain, after solvent evaporation, the requisite 2,6-dichloro-3-vinyl-pyridine product of Scheme 1, step D.

In scheme 1, step E, subsequent hydroboration of the vinyl moiety of 2,6-dichloro-3-vinyl-pyridine, the product of Scheme 1, step D, is well described in the art, and may be accomplished by heating a mixture of about 1 equivalent 2,6-dichloro-3-vinyl-pyridine with about 1.4 to 5 equivalents of 9-borabicyclo[3.3.1]nonane at about 45° C. for about 2 h. The resulting mixture may be treated with aqueous NaOH and H$_2$O$_2$. The resulting reaction product may be isolated by techniques well known in the art, such as extraction and column chromatography. For example, the reaction mixture may be diluted with a suitable organic solvent, such as EtOAc or DCM, the phases may be separated, the organic extract may be washed with saturated aqueous NaCl, dried over MgSO$_4$, filtered, and the filtrate may be concentrated under reduced pressure. The resulting residue may be subjected to flash chromatography over silica gel, eluting with a suitable organic solvent mixture, such as about 1:0 to about 1:1 cyclohexane and EtOAc, to obtain, after solvent evaporation, the requisite 2-(2,6-dichloro-3-pyridyl)ethanol.

Alternatively, in Scheme 1, step F, a Suzuki cross-coupling reaction of 2-[(E)-2-ethoxyvinyl]-4,4,5,5-tetramethyl-1,3,2-dioxaborolane and 2,6-dichloro-3-iodopyridine may be accomplished similarly as depicted in Scheme 1, step D, to obtain 2,6-dichloro-3-[(E)-2-ethoxyvinyl]pyridine. Subsequent O-dealkylation with in situ reduction of the aldehyde to the alcohol may be accomplished as is well known in the art for vinyl ethers, as shown in Scheme 1, step G. For example, about 1 equivalent of 2,6-dichloro-3-[(E)-2-ethoxyvinyl]pyridine, the product of Scheme 1, step F, in a polar organic solvent, such as acetone or 1,4-dioxane, may be treated with about 4-6 equivalents of an aqueous mineral acid, such as HCl, and the resulting mixture may be heated to about 60° C. for 3-8 h. The resulting aldehyde may be may be recovered by techniques well known in the art, such as extraction. For example, the reaction mixture may be diluted with a suitable organic solvent, such as EtOAc, and quenched with an aqueous solution of a mineral base, such as NaHCO$_3$. The resulting layers may be separated, the aqueous layer may be additionally extracted with EtOAc; the combined organic extracts may be washed with saturated aqueous NaCl, dried over MgSO$_4$, filtered, and the filtrate may be concentrated under reduced pressure. The resulting residue may be dissolved in a suitable mixture of polar organic solvents, such as MeOH and THF, and treated with about 1.3-1.8 equivalents of a suitable aluminum hydride or borohydride reducing agent, such as lithium aluminum hydride or NaBH$_4$. The resulting reaction product may be isolated by techniques well known in the art, such as extraction and column chromatography. For example, the reaction mixture may be diluted with a suitable organic solvent, such as EtOAc or DCM, the phases may be separated, the organic extract may be washed with saturated aqueous NaCl, dried over MgSO$_4$, filtered, and the filtrate may be concentrated under reduced pressure. The resulting residue may be subjected to flash chromatography over silica gel, eluting with a suitable organic solvent mixture, such as about 1:0 to about 2:3 cyclohexane and EtOAc, to obtain, after solvent removal, 2-(2,6-dichloro-3-pyridyl)ethanol, the product of Scheme 1, step G.

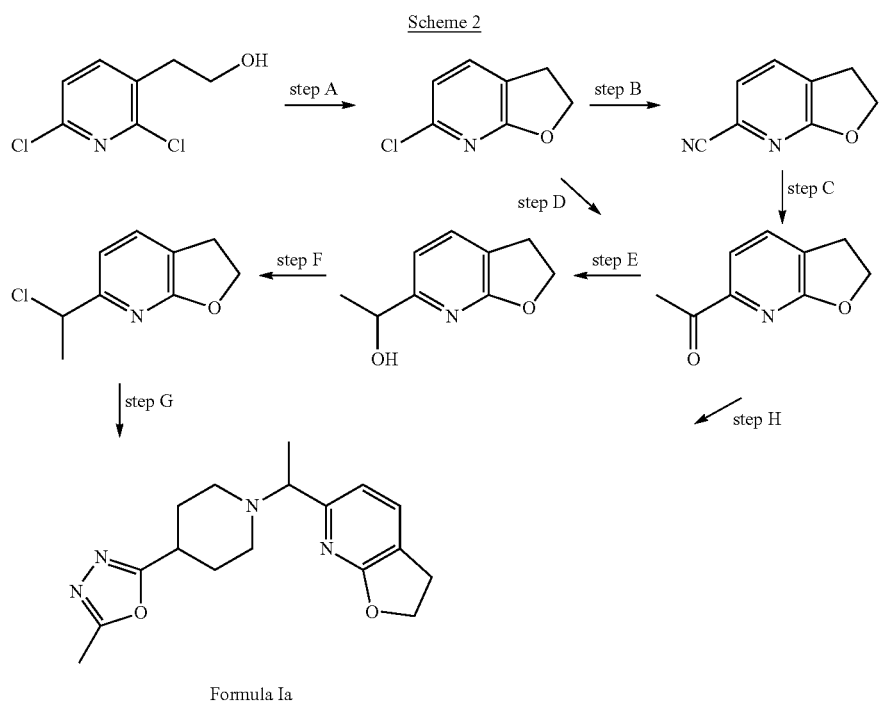

Scheme 2

Formula Ia

Scheme 2 depicts the synthesis of Formula Ia. In Scheme 2, step A, the skilled artisan will recognize that treatment of about 1 equivalent 2-(2,6-dichloro-3-pyridyl)ethanol with about 1.5 equivalents of a strong base, such as sodium-t-butoxide in a suitable solvent such as THF, 1,4-dioxane, or 2-methyl-2-butanol with heating at about 60° C. may yield the desired 6-chloro-2,3-dihydrofuro[2,3-b]pyridine (cf, Ondachi, Pauline W; Comins, Daniel L. *Journal of Organic Chemistry;* 75(5), 1706-16, 2010.) The resulting reaction product may be isolated by techniques well known in the art, such as extraction. For example, the reaction mixture may be diluted with a suitable mixture organic solvent, such as DCM or CHCl$_3$, and saturated aqueous salt, such as NH$_4$Cl. The resulting layers may be separated, the aqueous layer may be additionally extracted with the appropriate organic solvent, and the combined extracts may be washed with saturated aqueous NaCl, dried over MgSO$_4$, filtered, and the filtrate concentrated under reduced pressure, to obtain 6-chloro-2,3-dihydrofuro[2,3-b]pyridine, the product of Scheme 2, step A, suitable for additional use without additional purification.

In Scheme 2, step B, displacement of the 2-chloride with CN via transition-metal catalysis is well known in the literature. For example, a mixture of about 1 equivalent 6-chloro-2,3-dihydrofuro[2,3-b]pyridine, about 0.1-0.5 equivalents of potassium ferrocyanide trihydrate and about 0.5 equivalents of potassium acetate in a suitable organic solvent, such as 1,4-dioxane, THF, DMF, or DMSO, containing about 20% water and about 0.025-0.05 equivalents of a suitable palladium source, such as allyl(2-di-tert-butylphosphino-2',4',6'-triisopropyl-1,1'-biphenyl)palladium(II) triflate and a about 0.025-0.05 equivalents of a suitable ligand, such as 2-di-tert-butylphosphino-2',4',6'-triisopropylbiphenyl, may be heated to about 100° C. for about 12-24 h. The resulting reaction product may be isolated by techniques well known in the art, such as extraction and column chromatography. For example, the reaction mixture may be diluted with a suitable organic solvent, such as EtOAc or DCM, and water, the phases may be separated, the organic extract may be washed with saturated aqueous NaCl, dried over MgSO$_4$, filtered, and the filtrate may be concentrated under reduced pressure. The resulting residue may be subjected to flash chromatography over silica gel, eluting with a suitable organic solvent mixture, such as about 1:0 to about 2:3 cyclohexane and EtOAc, to obtain, after solvent removal, 2,3-dihydrofuro[2,3-b]pyridine-6-carbonitrile, the product of Scheme 2, step B.

Conversion of the cyano moiety to the corresponding methyl ketone may be accomplished by treatment with a Grignard or organolithium reagent, as is well known in the art. For example, in Scheme 2, step C, about 1 equivalent of 2,3-dihydrofuro[2,3-b]pyridine-6-carbonitrile, dissolved in a suitable organic solvent, such as Et$_2$O, THF or 1,4-dioxane, may be treated with about 2 equivalents of methylmagnesium bromide solution in Et$_2$O at about 0° C. for about 1-4 h. The resulting reaction product may be isolated by techniques well known in the art, such as extraction and column chromatography. For example, the reaction mixture may be diluted with a suitable organic solvent, such as EtOAc or DCM, and water, the phases may be separated, the organic extract may be washed with saturated aqueous NaCl, dried over MgSO$_4$, filtered, and the filtrate may be concentrated under reduced pressure. The resulting residue may be subjected to flash chromatography over silica gel, eluting with a suitable organic solvent mixture, such as about 1:0 to about 2:3 cyclohexane and EtOAc, to obtain, after solvent removal, 1-(2,3-dihydrofuro[2,3-b]pyridin-6-yl)ethanone, the product of Scheme 2, step C.

Alternatively, in Scheme 2, step D, 6-chloro-2,3-dihydrofuro[2,3-b]pyridine may be converted to 1-(2,3-dihydrofuro [2,3-b]pyridin-6-yl)ethanone under transition-metal catalysis. For example, about 1 equivalent of 6-chloro-2,3-dihydrofuro[2,3-b]pyridine and about 3 equivalents ethylene glycol monovinylether may be heated to about 110-170° C.

in a suitable polar organic solvent, such as ethylene glycol or DMSO, containing about 0.05 equivalents of a suitable transition metal-ligand complex, such as bis(triphenylphosphine)palladium(II) dichloride or [1,3-bis(diphenylphosphino)-propane]palladium(II) dichloride, and about 3-3.5 equivalents of an appropriate non-nucleophilic amine, such as TEA or DIPEA, for about 30-240 min. The resulting mixture may be concentrated under reduced pressure and treated with excess aqueous mineral acid, such as HCl, for about 5 min-2 h. The resulting reaction product may be isolated by techniques well known in the art, such as extraction. For example, the reaction mixture may be diluted with water and extracted with an appropriate organic solvent, such as DCM, CHCl$_3$, or EtOAc. The combined organic extracts may be washed with saturated aqueous NaCl, dried over MgSO$_4$, filtered, and the filtrate may be concentrated under reduced pressure, to give 1-(2,3-dihydrofuro[2,3-b]pyridin-6-yl)ethanone, the product of Scheme 2, step D, suitable for additional use without additional purification.

The skilled artisan will recognize that reduction of the ketone may be accomplished under a wide variety of conditions, such as with non-stereoselective aluminum hydrides or borohydrides, or with enantioselective reducing agents, such as enzymatic reductions, to obtain either racemic or enantioselective carbinol. For example, in Scheme 2, step E, treatment of about 1 equivalent of 1-(2,3-dihydrofuro[2,3-b]pyridin-6-yl)ethanone with an excess of an enzymatic enantioselective chiral reducing agent, such as ketoreductase P3-C12 enzyme, and a ketoreductase recycling mix may give an enantiomerically-enriched mixture of 1-(2,3-dihydrofuro[2,3-b]pyridin-6-yl)ethanol. The resulting reaction product may be isolated by techniques well known in the art, such as extraction and column chromatography. For example, the reaction mixture may be diluted with a suitable organic solvent, such as EtOAc or DCM, and water, the phases may be separated, the organic extract may be washed with saturated aqueous NaCl, dried over MgSO$_4$, filtered, and the filtrate may be concentrated under reduced pressure. The resulting residue may be subjected to flash chromatography over silica gel, eluting with a suitable organic solvent mixture, such as about 1:1 to about 0:1 iso-hexane and Et$_2$O, to obtain, after solvent removal, the separated enantiomers of 1-(2,3-dihydrofuro[2,3-b]pyridin-6-yl)ethanol, the product of Scheme 2, step E. The skilled artisan will recognize that resolution of the racemic or enantiomerically-enriched product mixture may additionally be accomplished via separation by column and/or chiral chromatography.

In Scheme 2, step F, conversion of the carbinol to the alkyl chloride may be accomplished under a variety of $S_N2$-type chlorinating conditions well known in the art. For example, about 1 equivalent of 1-(2,3-dihydrofuro[2,3-b]pyridin-6-yl)ethanol dissolved in a suitable organic solvent, such as DCM, and containing about 2.5 equivalents of a suitable non-nucleophilic amine base, such as TEA or DIPEA, may be treated with about 2 equivalents of methanesulfonyl chloride at about 0° C. to RT for about 24 h to 7 days. The resulting reaction product may be isolated by techniques well known in the art, such as extraction and column chromatography. For example, the reaction mixture may be diluted with a suitable organic solvent, such as EtOAc or DCM, and saturated aqueous NaHCO$_3$, the phases may be separated, the organic extract may be washed with saturated aqueous NaCl, dried over MgSO$_4$, filtered, and the filtrate may be concentrated under reduced pressure. The resulting residue may be subjected to flash chromatography over silica gel, eluting with a suitable organic solvent mixture, such as about 7:3 to about 1:1 iso-hexane and Et$_2$O, to obtain, after solvent removal, the racemic mixture of 6-(1-chloroethyl)-2,3-dihydrofuro[2,3-b]pyridine, the product of Scheme 2, step F. The skilled artisan will recognize that resolution of the racemic or enantiomerically-enriched product mixture may additionally be accomplished via separation by column and chiral chromatography, including SFC methods.

Scheme 2, step G depicts the preparation of Formula Ia. Chloride displacement of 6-(1-chloroethyl)-2,3-dihydrofuro[2,3-b]pyridine with an amine nucleophile under basic conditions is well known in the art. For example, a mixture of about 1 equivalent of 6-(1-chloroethyl)-2,3-dihydrofuro[2,3-b]pyridine and about 2 equivalents of an appropriately substituted piperidine (e.g., 4-(5-methyl-1,3,4-oxadiazol-2-yl)piperidine) may be heated thermally or heated/irradiated under microwave conditions in an appropriate organic solvent, such as ACN, 1,4-dioxane, DMF, or DMSO, at about 100-130° C. for about 90-240 min. The resulting reaction product may be isolated by techniques well known in the art, such as extraction and column chromatography. For example, the reaction mixture may be diluted with a suitable organic solvent, such as EtOAc or DCM, and saturated aqueous NH$_4$Cl, the phases may be separated, the organic extract may be washed with saturated aqueous NaCl, dried over MgSO$_4$, filtered, and the filtrate may be concentrated under reduced pressure. The resulting residue may be subjected to flash chromatography over silica gel, eluting with a suitable organic solvent mixture, such as about 1:0 to about 9:1 DCM and MeOH, with additional purification by SFC chiral chromatography over C-18 silica gel, eluting with a suitable mixture of an alcoholic solvent, such as isopropanol, containing a non-nucleophilic amine, such as DMEA or TEA, in CO$_2$, for example, about 1:9 to 1:4 isopropanol containing about 0.2% DMEA in CO$_2$, to obtain, after solvent removal, the separated enantiomers of 6-[1-[4-(5-methyl-1,3,4-oxadiazol-2-yl)-1-piperidyl]ethyl]-2,3-dihydrofuro[2,3-b]pyridine, the product of Scheme 2, step G.

Alternatively, as is well appreciated in the art, Formula Ia may be prepared via reductive amination techniques, as shown in Scheme 2, step H. For example, a mixture of about 1 equivalent of 1-(2,3-dihydrofuro[2,3-b]pyridin-6-yl)ethanone and about 2 equivalents of an appropriately substituted piperidine (e.g., 4-(5-methyl-1,3,4-oxadiazol-2-yl)piperidine) in a suitable organic solvent, such as MeOH, EtOH, THF, 1,4-dioxane, DCM, dichloroethane, or CHCl$_3$, containing about 2 equivalents of a suitable Lewis acid, such as titanium(IV) isopropoxide, zinc(II) chloride or zinc(II) acetate. The reaction mixture may be stirred at about RT to about reflux, and about 3 equivalents of an appropriate reducing agent, such as sodium borohydride, sodium cyanoborohydride, or sodium triacetoxyborohydride is added. The reactions mixture may be heated to about 40° C. to about reflux for about 12-24 h. The resulting reaction product may be isolated by techniques well known in the art, such as extraction and chiral column chromatography. For example, the reaction mixture may be diluted with a suitable organic solvent, such as EtOAc or DCM, and saturated aqueous NH$_4$Cl, the phases may be separated, the organic extract may be washed with saturated aqueous NaCl, dried over MgSO$_4$, filtered, and the filtrate may be concentrated under reduced pressure. The resulting residue may be subjected to flash chiral chromatography over C-18 silica gel, eluting with a suitable mixture of about aqueous NH$_4$HCO$_3$ in ACN, with additional purification by SFC chiral chromatography over C-18 silica gel, eluting with a suitable mixture of an alcoholic solvent, such as isopropanol, containing a non-nucleophilic amine, such as DMEA or TEA, in CO$_2$, for example, about 1:9 to 1:4 isopropanol containing about 0.2% DMEA in CO$_2$, to obtain, after solvent removal, the separated enantiomers of 6-[1-[4-(5-methyl-1,3,4-oxadiazol-2-yl)-1-piperidyl]ethyl]-2,3-dihydrofuro[2,3-b]pyridine, the product of Scheme 2, step H. The skilled artisan will recognize that any chiral materials may be separated as necessary at any step in the synthesis of Scheme 2 via chiral chromatography, including SFC.

aprotic, polar solvent may be added. The resulting mixture may be stirred for about 60-180 min. The resulting crude reaction product may be recovered by techniques well known in the art, such as extraction methods. For example, the cooled reaction mixture may be diluted with an appropriate aqueous salt solution, such as NH4Cl, and extracted with an appropriate organic solvent, such as DCM, Et$_2$O, or EtOAc. The combined organic extracts may be washed with saturated aqueous NaCl, dried over MgSO$_4$, filtered, and the

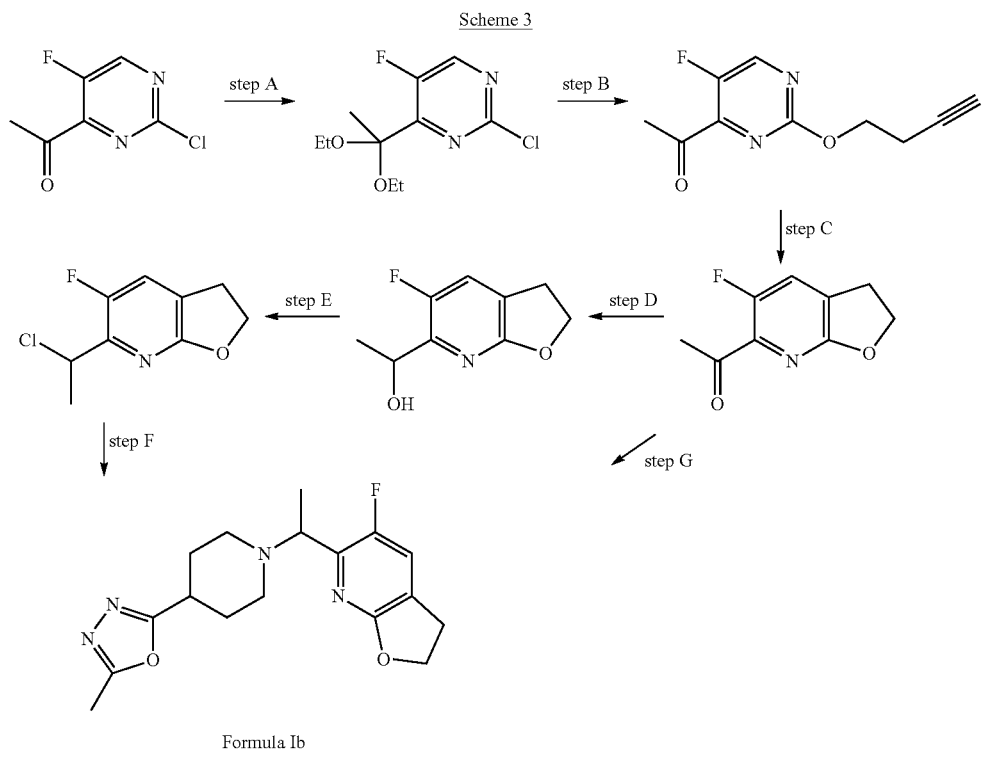

Formula Ib

Scheme 3 depicts the synthesis of Formula Ib. In Scheme 3, step A, about 1 equivalent of 1-(2-chloro-5-fluoro-pyrimidin-4-yl)ethanone (U.S. Pat. No. 8,629,270) may be treated with about 0.25-0.5 equivalents of trifluoromethanesulfonic acid in triethylorthoformate at RT for about 48-96 h. The resulting reaction product may be isolated by techniques well known in the art, such as evaporation and column chromatography. For example, the reaction mixture may be concentrated under reduced pressure, and the resulting residue may be subjected to flash chromatography over silica gel, eluting with a suitable organic solvent mixture, such as about 95:5 to about 85:15 iso-hexane and Et$_2$O, to obtain, after solvent removal, 2-chloro-4-(1,1-diethoxyethyl)-5-fluoro-pyrimidine, the product of Scheme 3, step A.

Nucleophilic displacement of the chloride moiety in 2-chloro-4-(1,1-diethoxyethyl)-5-fluoro-pyrimidine with subsequent deprotection to the ketone in the 4-position may be accomplished in 2 steps sequentially, as is well documented in the art, without isolation of the chloride displacement product. For example, about 1 equivalent of 3-butyn-1-ol dissolved in an aprotic, polar organic solvent, such as THF or 1,4-dioxane, may be treated with about 1 equivalent of a 60% dispersion of NaH in mineral oil for about 30 min-2 h, and a solution of about 0.95-1 equivalent of 2-chloro-4-(1,1-diethoxyethyl)-5-fluoro-pyrimidine dissolved in similar filtrate concentrate under reduced pressure. The resulting residue may be dissolved in an appropriate polar organic solvent, such as THF or 1,4-dioxane, and treated with excess mineral acid, such as HCl, and stirred for about 3-24 h. The resulting reaction product may be recovered by techniques well known in the art, such as filtration. For example, the reaction mixture may be concentrated to partial volume under reduced pressure, the resulting residue may be triturated with a suitable non-polar organic solvent such as hexanes or cyclohexane, and the resulting precipitate may be collected by filtration to afford 1-(2-but-3-ynoxy-5-fluoropyrimidin-4-yl)ethanone, the product of Scheme 3, step B.

Intramolecular cyclization via an inverse-electron-demand hetero-Diels-Alder-type reaction with subsequent cycloreversion of pyrimidine alkynes to obtain the corresponding tetrahydroazabenzofurans has been reported in the literature (see R. E. Martin, et al., *Eur. J. Org. Chem.* 2012, 47-52.) As such, in Scheme 3, step C, a solution of 1-(2-but-3-ynoxy-5-fluoro-pyrimidin-4-yl)ethanone in an appropriate high-boiling solvent, such as N-methylpyrrolidinone or sulfolane, may be heated to about 235° C. for about 30 min. The resulting reaction product may be isolated by techniques well known in the art, such as column chromatography. For example, the reaction mixture may be subjected to flash chromatography over silica gel, eluting with a suitable organic solvent mixture, such as about 7:3 to about 1:4 iso-hexane and MTBE, to obtain 1-(5-fluoro-2,3-dihydrofuro[2,3-b]pyridin-6-yl)ethanone, the product of Scheme 3, step C, after solvent evaporation.

Scheme 3, step D, may be accomplished under conditions similar to those described in Scheme 2, step E. Additionally, asymmetric reduction of the ketone to the corresponding chiral carbinol may be effected using an array of chiral catalysts, as is well appreciated in the art. For example, about 1 equivalent of 1-(5-fluoro-2,3-dihydrofuro[2,3-b] pyridin-6-yl)ethanone and about may be heated in a 5:2 complex of $HCO_2H$-TEA containing about 0.05-0.1 equivalents of a ruthenium-based chiral catalyst, for example, [N-[(1S,2S)-2-(amino-κN)-1,2-diphenylethyl]-4-methyl-benzenesulfonamidato-κN]chloro[(1,2,3,4,5,6-f)-1-methyl-4-(1-methylethyl)benzene]-ruthenium. The mixture may be heated to about 35° C. for about 2-4 h under nitrogen, and the resulting reaction product may be isolated by techniques well known in the art, such as extraction and column chromatography. For example, the reaction mixture may be diluted with a suitable organic solvent, such as EtOAc or DCM, and saturated aqueous $NaHCO_3$, the phases may be separated, the organic extract may be washed with saturated aqueous NaCl, dried over $Na_2SO_4$, filtered, and the filtrate may be concentrated under reduced pressure. The resulting residue may be subjected to flash chromatography over silica gel, eluting with a suitable organic solvent mixture, such as about 1:1 hexane and EtOAc, to obtain, after solvent removal, the separated enantiomers of 1-(5-fluoro-2,3-dihydrofuro[2,3-b]pyridin-6-yl)ethanol, the product of Scheme 3, step D.

In Scheme 3, steps E-F, the separated enantiomers of Formula Ib may be prepared similarly to the conditions described in Scheme 2, steps F-G. Alternatively, in Scheme 3, step G, the separated enantiomers of Formula Ib may be prepared from 1-(5-fluoro-2,3-dihydrofuro[2,3-b]pyridin-6-yl)ethanone via reductive amination similar to Scheme 2, step H. As in Scheme 2, the skilled artisan will recognize that chiral materials may be separated using standard techniques as necessary at any step in the synthesis in Scheme 3.

PREPARATIONS AND EXAMPLES

The following Preparations and Examples further illustrate the invention and represent typical synthesis of compounds of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

LC-ES/MS is performed on an AGILENT©HP1100 liquid chromatography system. Electrospray mass spectrometry measurements (acquired in positive and/or negative mode) are performed on a Mass Selective Detector quadrupole mass spectrometer interfaced to the HP1100 HPLC. LC-MS conditions (low pH): column: PHENOMENEX© GEMINI©NX C18 2.1×50 mm 3.0 μm; gradient: 5-100% B in 3 min, then 100% B for 0.75 min column temperature: 50° C.+/−10° C.; flow rate: 1.2 mL/min; Solvent A: deionized water with 0.1% HCOOH; Solvent B: ACN with 0.1% formic acid; wavelength 214 nm. Alternate LC-MS conditions (high pH): column: XTERRA©MS C18 columns 2.1×50 mm, 3.5 μm; gradient: 5% of solvent A for 0.25 min, gradient from 5% to 100% of solvent B in 3 min and 100% of solvent B for 0.5 min or 10% to 100% of solvent B in 3 min and at 100% of solvent B for 0.75 min; column temperature: 50° C.+/−10° C.; flow rate: 1.2 mL/min; Solvent A: 10 mM $NH_4HCO_3$ pH 9; Solvent B: ACN; wavelength: 214 nm.

Preparative reversed phase chromatography is performed on an AGILENT® 1200 LC-ES/MS equipped with a Mass Selective Detector mass spectrometer and a LEAP® autosampler/fraction collector. High pH methods are run on a 75×30 mm PHENOMENEX© GEMINI©-NX, 5μ particle size column with a 10×20 mm guard. Flow rate of 85 mL/min. Eluent is 10 mM ammonium bicarbonate (pH 10) in acetonitrile unless noted otherwise.

NMR spectra are performed on a Bruker AVIII HD 400 MHz NMR Spectrometer, obtained as $CDCl_3$ or DMSO solutions reported in ppm, using residual solvent [$CDCl_3$, 7.26 ppm; $(CD_3)_2SO$, 2.05 ppm] as reference standard. When peak multiplicities are reported, the following abbreviations may be used: s (singlet), d (doublet), t (triplet), q (quartet), m (multiplet), br-s (broad singlet), dd (doublet of doublets), dt (doublet of triplets). Coupling constants (J), when reported, are reported in hertz (Hz).

Preparation 1 diethyl 2-(2,6-dichloro-3-pyridyl)propanedioate

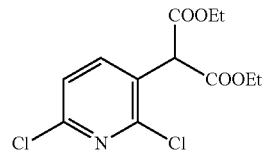 [SMILES: CCOC(=O)C(C(=O)OCC)c1ccc(Cl)nc1Cl]

Scheme 1, step A: A mixture of diethyl malonate (17.8 mL, 117 mmol), 2,6-dichloro-3-iodopyridine (21.8 g, 78.1 mmol), picolinic acid (1.2 g, 10.1 mmol), CuI (0.8 g, 4.3 mmol) and $Cs_2CO_3$ (74.8 g, 229.6 mmol) in 1,4-dioxane (200 mL), under nitrogen, is stirred at 80° C. for 6 h. The reaction mixture is cooled to RT and saturated aqueous $NH_4Cl$ (150 mL) is added. The resulting mixture is extracted twice with EtOAc, and the combined organic extracts are washed sequentially with saturated aqueous $NH_4Cl$ and saturated aqueous NaCl solution. The organic extracts are dried over $MgSO_4$, filtered, and the filtrate is evaporated under reduced pressure to afford the title compound (29.4 g, 93% yield) as a brown oil, which is suitable for use without further purification. ES/MS ($^{35}Cl/^{37}Cl$) m/z: 306/308 (M+H).

Preparation 2

2-(2,6-dichloro-3-pyridyl)acetic acid

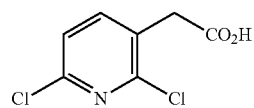 [SMILES: O=C(O)Cc1ccc(Cl)nc1Cl]

Scheme 1, step B: A solution of diethyl 2-(2,6-dichloro-3-pyridyl)propanedioate (1.2 g, 2.5 mmol) in a 5 M aqueous solution of HCl (11 mL) is heated at reflux for 24 h. The reaction cooled to RT and the resulting white precipitate is collected by filtration to afford the title compound (362 mg, 64% yield) as a white powder. ES/MS ($^{35}$Cl/$^{37}$Cl) m/z: 206/208 (M+H).

Preparation 3

2,6-dichloro-3-[(E)-2-ethoxyvinyl]pyridine

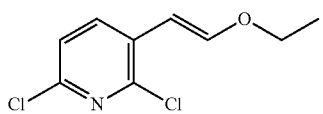

Scheme 1, step F: To a 1 necked round bottom flask, with stirrer, and air condenser, under nitrogen, is added 2,6-dichloro-3-iodo-pyridine (1.0 g, 3.8 mmol), 2-[(E)-2-ethoxyvinyl]-4,4,5,5-tetramethyl-1,3,2-dioxaborolane (0.9 g, 4.8 mmol), Cs$_2$CO$_3$ (3.75 g, 11.5 mmol), 1,4-dioxane (19.2 mL), and water (4.26 mL). This reaction mixture is purged 3 times alternating between vacuum and nitrogen, and [1,1' bis(diphenylphosphino) ferrocene]dichloropalladium(II) (0.2 g) is added. The resulting mixture is stirred for 3 hr at 90° C., the reaction is poured onto saturated aqueous NH$_4$Cl, and the aqueous mixture is extracted three times with EtOAc. The combined organic extracts are dried over MgSO$_4$, filtered, and the filtrate is concentrated under reduced pressure. The resulting residue is purified by flash chromatography over silica gel, eluting with a gradient of 0-100% EtOAc in cyclohexane, to afford the title compound (748 mg, 89% yield), after solvent evaporation of the desired chromatographic fractions. $^1$H NMR (300 MHz, CDCl$_3$): δ 1.37 (m, 3H), 3.97 (m, 2H), 5.97 (m, 1H), 6.99 (m, 1H), 7.16 (m, 1H), 7.60 (m, 1H).

Preparation 4

2,6-dichloro-3-vinyl-pyridine

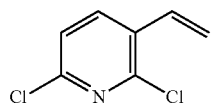

Scheme 1, step D: To a round bottom flask is added 2,6-dichloro-3-iodo-pyridine (6.3 g, 22.9 mmol), potassium vinyltrifluoroborate (3.09 g, 23 mmol), bis(triphenlyphosphine)palladium(II) dichloride (327 mg, 0.46 mmol) and Na$_2$CO$_3$ (4.85 g, 45.7 mmol). The flask is evacuated and back-filled with nitrogen three times. EtOH (75.1 mL) is added and the flask is again evacuated and back-filled with nitrogen three times. The reaction mixture is heated at 90° C. overnight, diluted with EtOAc and water, the phases are separated, and the aqueous phase is extracted three times with EtOAc. The organic extracts are combined, dried over MgSO$_4$, filtered, and the filtrate is concentrated under reduced pressure. The resulting residue is purified by flash chromatography over silica gel, eluting with a gradient of 0-100% EtOAc in cyclohexane, to obtain the title compound (3.0 g, 69% yield), after solvent evaporation of the desired chromatographic fractions. $^1$H NMR (300 MHz, CDCl$_3$): δ 5.53 (m, 1H), 5.78 (m, 1H), 6.97 (m, 1H), 7.26 (m, 1H), 7.82 (m, 1H).

Preparation 5

2-(2,6-dichloro-3-pyridyl)ethanol

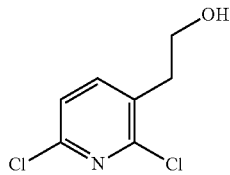 [SMILES: OCCc1ccc(Cl)nc1Cl]

Scheme 1, step C: A solution of 2-(2,6-dichloro-3-pyridyl)acetic acid (8.1 g, 37 mmol) in THF (100 mL) is cooled in an ice-bath. A 1 M solution of BH$_3$-THF complex in THF (55.5 mL, 55.5 mmol) is added slowly. The reaction mixture is stirred for 1 h, warmed to RT, and stirred for a further 20 h. MeOH (30 mL) is added cautiously, the resulting solution is stirred for 5 min, and concentrated under reduced pressure. The resulting residue is dissolved in MeOH and concentrated under reduced pressure again to afford the title compound as a thick brown oil (7.7 g, 98% yield), suitable for use without additional purification. ES/MS ($^{35}$Cl/$^{37}$Cl) m/z: 192/194 (M+H).

Alternate Procedure for Preparation 5

Scheme 1, step G: To a 1 necked round bottom flask, with stirrer and air condenser, under nitrogen, is added 2,6-dichloro-3-[(E)-2-ethoxyvinyl]pyridine (748 mg, 3.4 mmol) to acetone (17.1 mL) and a 2M aqueous solution of HCl (8.6 mL) is added. The resulting mixture is heated at 60° C. with stirring for 3.5 h. The resulting mixture is cooled to RT, diluted with EtOAc, and quenched with saturated aqueous NaHCO$_3$. The resulting aqueous mixture is extracted three times with EtOAc, the combined organic extracts are dried over MgSO$_4$, filtered, and the filtrate is concentrated under reduced pressure. The resulting residue is dissolved in MeOH (8.6 mL) and THF (4.9 mL), and NaBH$_4$ (195 mg) is added portion-wise over 5 min. The reaction mixture is stirred at RT for 40 min, quenched with water, extracted three times with EtOAc, and the combined organic extracts are washed with saturated aqueous NaCl, dried over MgSO$_4$, filtered, and the filtrate is concentrated under reduced pressure. The resulting residue is purified by flash chromatography over silica gel, eluting with a gradient of 0-60% EtOAc in cyclohexane, to obtain the title compound (315 mg, 47% yield), after solvent evaporation of the desired chromatographic fractions. ES/MS m/z: 193 (M+H).

Alternate Procedure for Preparation 5

Scheme 1, step E: To a flask was added 2,6-dichloro-3-vinyl-pyridine (3 g, 17.5 mmol) and THF (1.5 mL) at RT. The mixture was stirred in an ice-water bath and a 0.5M solution of 9-borabicyclo[3.3.1]nonane in THF (49.1 mL) is added dropwise over 2 min. The reaction mixture is stirred in a 45° C. heating block for 2 h. The reaction mixture is stirred in an ice-water bath, and 2N aqueous NaOH (26.3 mL) is added dropwise over 5 min, followed by a 35% aqueous solution of H$_2$O$_2$ (4.87 mL) over 2 min, and the resulting reaction mixture is stirred at RT for 2 h. The reaction mixture is diluted with water and extracted three times with EtOAc, the combined organic extracts are washed with saturated aqueous Na$_2$S$_2$O$_3$-5H$_2$O solution, dried over Na$_2$SO$_4$, and concentrated under reduced pressure. The resulting residue is purified by flash chromatography over silica gel, eluting with 0-50% EtOAc/cyclohexane, to obtain the title compound (1.8 g, 55% yield) after solvent evaporation of the desired chromatographic fractions. ES/MS m/z: 193 (M+H).

Preparation 6

6-chloro-2,3-dihydrofuro[2,3-b]pyridine

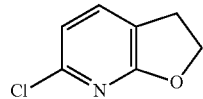

Scheme 2, step A: A solution of 2-(2,6-dichloro-3-pyridyl)ethanol (10.8 g, 56.3 mmol) and potassium tert-butoxide (9.5 g, 84.5 mmol) in 2-methyl-2-butanol (200 mL) is heated at 60° C. for 2 h. The reaction mixture is cooled to RT, concentrated to partial volume under reduced pressure, and the resulting mixture is diluted with CHCl$_3$ and saturated aqueous NH$_4$Cl. The resulting layers are separated, the aqueous phase is additionally extracted twice with CH$_3$Cl, the combined organic extracts are dried over MgSO$_4$, filtered, and the filtrate is concentrated under reduced pressure to obtain the title compound as brown oil (8.7 g, 84% yield), which solidified upon standing at RT, of sufficient purity for use without additional purification. ES/MS ($^{35}$Cl/$^{37}$Cl) m/z: 156/158 (M+H).

Preparation 7

2,3-dihydrofuro[2,3-b]pyridine-6-carbonitrile

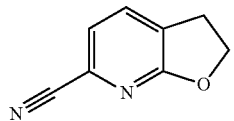 [SMILES: N#Cc1ccc2c(n1)OCC2]

Scheme 2, step B: To a round bottom flask is added 6-chloro-2,3-dihydrofuro[2,3-b]pyridine (1.1 g, 7.2 mmol), 2-di-tert-butylphosphino-2',4',6'-triisopropylbiphenyl (126 mg, 0.3 mmol), allyl(2-di-tert-butylphosphino-2',4',6'-triisopropyl-1,1'-biphenyl)palladium(II) triflate (208 mg, 0.3 mmol), KOAc (353 mg, 3.6 mmol) and potassium ferrocyanide trihydrate (492 mg, 1.1 mmol). To the mixture is added water (2.2 mL) and 1,4-dioxane (7.2 mL) and nitrogen is bubbled through the mixture for 10 min at RT. The reaction mixture is stirred in a 100° C. heating block overnight. The reaction mixture is cooled to RT, diluted with EtOAc, quenched with water, the phases are separated, and the aqueous phase is additionally extracted three times with EtOAc. The combined organic extracts are washed with saturated aqueous NaCl, dried over MgSO$_4$, filtered, and the filtrate is concentrated under reduced pressure. The resulting residue is purified by flash chromatography over silica gel, eluting with a gradient of 0-40% EtOAc in cyclohexane, to obtain the title compound (600 mg, 57% yield), after solvent evaporation of the desired chromatographic fractions. ES/MS m/z: 147 (M+H).

Preparation 8

1-(2,3-dihydrofuro[2,3-b]pyridin-6-yl)ethanone

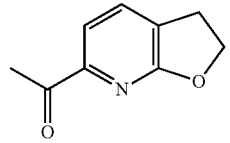

Scheme 2, step D: A mixture of 6-chloro-2,3-dihydrofuro[2,3-b]pyridine (8.6 g, 47.4 mmol), ethylene glycol monovinylether (13 mL, 145 mmol), [1,3-bis(diphenylphosphino)propane]palladium(II) dichloride (1.4 g, 2.4 mmol) and TEA (23 mL, 165 mmol) in ethylene glycol (100 mL) is heated to 160° C. for 1 h. The resulting mixture is cooled and concentrated under reduced pressure. An aqueous solution of 5 N HCl (50 mL) is added to the resulting residue, the mixture is stirred for 10 min, and extracted three times with DCM. The combined organic extracts are concentrated under reduced pressure and the resulting residue is slurried in EtOAc. The resulting mixture is filtered and the filtrate is washed three times with water. The organic phase is dried over MgSO$_4$ and concentrated under reduced pressure to afford the title compound as brown oil, which slowly solidifies upon standing at RT (7.0 g, 82% yield), suitable for use without additional purification. ES/MS m/z: 164 (M+H).

Alternate Procedure for Preparation 8

Scheme 2, step C: To a flask is added 2,3-dihydrofuro[2,3-b]pyridine-6-carbonitrile (349 mg, 2.4 mmol) in THF (4.7 mL). A 3 M solution of methylmagnesium bromide in Et$_2$O (1.5 mL) is added at 0° C. and the resulting reaction mixture is stirred for 2 h. The mixture is quenched with saturated aqueous NH$_4$Cl and stirred for 20 min. The mixture is extracted three times with EtOAc, and the combined organic extracts are washed with saturated aqueous NaCl, dried over MgSO$_4$, filtered, and the filtrate is concentrated under reduced pressure. The resulting residue is purified by flash chromatography over silica gel, eluting with a gradient of 0-40% EtOAc in cyclohexane, to obtain the title compound (339 mg, 87% yield), after solvent evaporation of the desired chromatographic fractions. ES/MS m/z: 164 (M+H).

Preparation 9

(−)-1-(2,3-dihydrofuro[2,3-b]pyridin-6-yl)ethanol

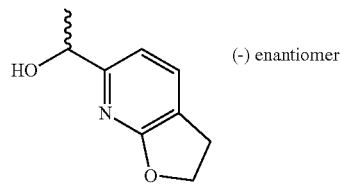

Scheme 2, step E: To a solution of 1-(2,3-dihydrofuro[2,3-b]pyridin-6-yl)ethanone (1.8 g, 11.2 mmol) in water (160 mL) and IPA (40 mL) is added KRED P3-C12 enzyme (0.9 g) and KRED recycle mix P (0.9 g). The reaction is stirred at 35° C. for 18 h and the resulting mixture is extracted three times with EtOAc. The combined organic extracts are washed sequentially with water and saturated aqueous NaCl, dried over MgSO$_4$, filtered, and the filtrate is concentrated under reduced pressure. The resulting residue is purified via flash chromatography over silica gel, eluting with a gradient of 50-100% Et$_2$O:iso-hexane, to afford the title compound (1.35 g, 73% yield) after solvent evaporation of the desired chromatographic fractions. ES/MS m/z: 166 (M+H). $[\alpha]_D^{20}$=−58.2° (c=1, MeOH). As used hereinabove, the terms "(−)" or "(−) enantiomer" for Preparation 9 refers to the enantiomer of Preparation 9 which has an optical rotation which is counterclockwise (or "(−)") at 20° C. and 589 nm with the noted concentration "c" (g/100 mL) in methanol.

Preparation 10

(+)-6-[1-chloroethyl]-2,3-dihydrofuro[2,3-b]pyridine

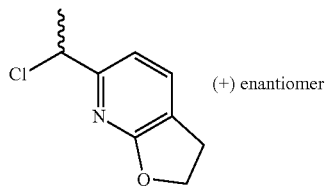

Scheme 2, step F: A solution of (−)-1-(2,3-dihydrofuro[2,3-b]pyridin-6-yl)ethanol (1.35 g, 8.2 mmol) and TEA (2.8 mL, 20 mmol) in DCM (35 mL) is cooled in an ice-bath and methane sulfonylchloride (1.2 mL, 15 mmol) is added drop-wise. The reaction is warmed to RT, stirred for 7 days, and quenched with saturated aqueous NaHCO$_3$ (20 mL). The mixture is poured through a phase separator cartridge, washing with DCM. After removing the solvent under reduced pressure, the resulting residue is purified by flash chromatography over silica gel, eluting with a gradient of Et$_2$O:iso-hexane, to afford the title compound (1.2 g, 76% yield) after solvent evaporation of the desired chromatographic fractions. ES/MS ($^{35}$Cl/$^{37}$Cl) m/z: 184/186 (M+H). $[\alpha]_D^{20}$=+88.20 (c=1, DCM). As used hereinabove, the terms "(+)" or "(+) enantiomer" for Preparation 10 refers to the enantiomer of Preparation 10 which has an optical rotation which is clockwise (or "(+)") at 20° C. and 589 nm with the noted concentration "c" (g/100 mL) in DCM.

Preparation 11

2-chloro-4-(1,1-diethoxyethyl)-5-fluoro-pyrimidine

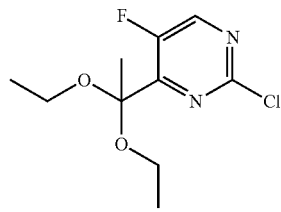 [SMILES: CCOC(C)(OCC)c1nc(Cl)ncc1F]

Scheme 3, step A: To a solution 1-(2-chloro-5-fluoro-pyrimidin-4-yl)ethanone (46.4 g, 266 mmol) in triethyl orthoformate (120 mL) is added trifluoromethanesulfonic acid (1 mL). The reaction is stirred for 72 h and concentrated in vacuo. The resulting residue is purified by flash chromatography over silica gel, eluting with a gradient of 5-15% Et$_2$O/iso-hexane, to afford the title compound (53.9 g, 70% yield) after solvent evaporations of the desired chromatographic fractions. ES/MS ($^{35}$Cl/$^{37}$Cl) m/z: 249/251 (M+H).

Preparation 12

1-(2-but-3-ynoxy-5-fluoro-pyrimidin-4-yl)ethanone

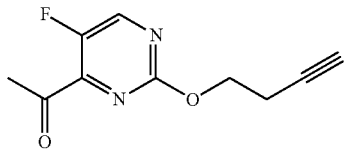

Scheme 3, step B: To an ice-bath cooled solution of 3-butyn-1-ol (17 mL, 218 mmol) in THF (400 mL) is added portion wise a suspension of 60% NaH in mineral oil (8.7 g, 218 mmol). The resulting mixture is stirred at RT for 1 h and 2-chloro-4-(1,1-diethoxyethyl)-5-fluoro-pyrimidine (53.9 g, 217 mmol) in THF (200 mL) is added dropwise. The dark-red mixture is stirred for 90 min and quenched with saturated aqueous NH$_4$Cl. The aqueous mixture is extracted three times with EtOAc, the combined extracts are washed with saturated aqueous NaCl, dried over MgSO$_4$, filtered, and the filtrate is concentrated under reduced pressure. The resulting residue in dissolved in THF (400 mL) and aqueous 2 N HCl (100 mL) is added. The resulting mixture is stirred for 3 h and concentrated under reduced pressure. The resulting precipitate is collected by filtration and triturated with cyclohexane to afford, after filtration, the title compound (39.6 g, 85% yield). ES/MS m/z: 209 (M+H).

Preparation 13

1-(5-fluoro-2,3-dihydrofuro[2,3-b]pyridin-6-yl)ethanone

Scheme 3, step C: A solution of 1-(2-but-3-ynoxy-5-fluoro-pyrimidin-4-yl)ethanone (3.25 g, 14.8 mmol) in sulfolane (20 mL) is heated to 235° C. for 30 min. The mixture is purified by flash chromatography over silica gel, eluting with a gradient of 40-80% MTBE:iso-hexane, to obtain a yellow oil after solvent evaporation of the desired chromatographic fractions. The resulting residue is further purified by flash chromatography over silica gel, eluting with a gradient of 30-50% MTBE:iso-hexane, to afford the title compound as a yellow solid (739 mg, 27% yield) after solvent evaporation of the desired chromatographic fractions. ES/MS m/z: 182 (M+H).

Preparation 14

1-(5-fluoro-2,3-dihydrofuro[2,3-b]pyridin-6-yl)ethanol

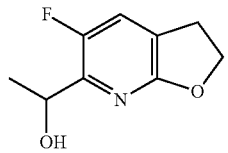

Scheme 3, step D: A solution of 1-(5-fluoro-2,3-dihydrofuro[2,3-b]pyridin-6-yl)ethanone (904 mg, 4.9 mmol) in THF (30 mL) and EtOH (5 mL) is cooled in an ice-bath. NaBH$_4$ (194 mg, 5.1 mmol) is added and the mixture stirred for 1.5 h. The reaction is quenched by careful addition of saturated aqueous NH$_4$Cl and concentrated under reduced pressure. Water and DCM are sequentially added to the resulting residue and the resulting biphasic mixture is filtered through a phase separator cartridge. The separated DCM filtrate is concentrated under reduced pressure to afford the title compound (845 mg, 94% yield). ES/MS m/z: 184 (M+H).

Preparation 15

6-(1-chloroethyl)-5-fluoro-2,3-dihydrofuro[2,3-b]pyridine

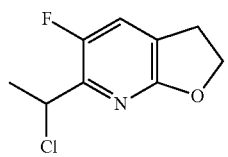

Scheme 3, step E: A solution of 1-(5-fluoro-2,3-dihydrofuro[2,3-b]pyridin-6-yl)ethanol (845 mg, 4.6 mmol) and DIPEA (1.8 mL, 10 mmol) in DCM (20 mL) is cooled in an ice bath and methane sulfonylchloride (0.8 mL, 10 mmol) is added drop-wise. The reaction is warmed to RT and stirred for 16 h. The mixture is diluted with DCM and quenched using saturated aqueous NaHCO$_3$ (20 mL). The mixture is poured through a phase separator cartridge, washing with DCM. The DCM phase is collected, concentrated under reduced pressure, and the resulting residue is purified by flash chromatography over silica gel, eluting with a gradient of 50-100% Et$_2$O:iso-hexane, to afford the title compound (858 mg, 83% yield) after solvent evaporation of the desired chromatographic fractions. ES/MS ($^{35}$Cl/$^{37}$Cl) m/z: 202.0/204 (M+H).

Preparation 16

(−)-1-(5-fluoro-2,3-dihydrofuro[2,3-b]pyridin-6-yl)ethanol

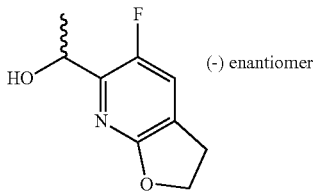

Scheme 3, step D: Combine 1-(5-fluoro-2,3-dihydrofuro[2,3-b]pyridin-6-yl)ethanone (3.419 g, 18.9 mmol) and [N-[(1S,2S)-2-(amino-κN)-1,2-diphenylethyl]-4-methylbenzenesulfonamidato-N]chloro[(1,2,3,4,5,6-η)-1-methyl-4-(1-methylethyl)benzene]-ruthenium (1.0 g, 1.6 mmol) in HCOOH-TEA 5:2 complex (30 mL) and purge with nitrogen for 5 min with stirring. Heat the resulting mixture to 35° C. for 2 h under N$_2$. Cool the reaction mixture and dilute with EtOAc and saturated aqueous NaHCO$_3$. Extract the mixture three times with EtOAc. Dry the combined organic extracts over Na$_2$SO$_4$, filter, and remove the solvent from the filtrate under reduced pressure. Purify the crude product by flash chromatography over silica gel, using a mixture of 50% EtOAc in hexanes, to afford the title compound (3.0 g, 87% yield) after solvent evaporation of the desired chromatographic fractions. ES/MS m/z: 184 (M+H). [α]$_D^{20}$=−16.80 (c=2, MeOH). As used hereinabove, the terms "(−)" or "(−) enantiomer" for Preparation 16 refers to the enantiomer of Preparation 16 which has an optical rotation which is counterclockwise (or "(−)") at 20° C. and 589 nm with the noted concentration "c" (g/100 mL) in methanol.

Preparation 17

(+)-6-[1-chloroethyl]-5-fluoro-2,3-dihydrofuro[2,3-b]pyridine

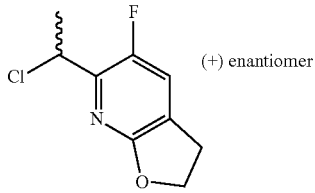

Scheme 3, step E: A solution of (−)-1-(5-fluoro-2,3-dihydrofuro[2,3-b]pyridin-6-yl)ethanol (3.0 g, 16.3 mmol) in DMF (75 mL) is treated dropwise with benzoyl chloride (2.9 mL, 25 mmol). The reaction mixture is stirred at RT for 16 h under nitrogen. The mixture is diluted with EtOAc and saturated aqueous NaHCO$_3$. Extract the mixture three times with EtOAc, dry the combined organic extracts over Na$_2$SO$_4$, filter, and remove the solvent from the filtrate under reduced pressure. Purify the crude product by flash chromatography over silica gel, using a gradient of 5% to 100% EtOAc in hexanes, to afford the title compound (3.1 g, 95% yield) after solvent evaporation of the desired chromatographic fractions. ES/MS ($^{35}$Cl/$^{37}$Cl) m/z: 202.0/204

(M+H). $[\alpha]_D^{20}$=+68.2° (c=0.2, DCM). As used hereinabove, the terms "(−)" or "(−) enantiomer" for Preparation 17 refers to the enantiomer of Preparation 17 which has an optical rotation which is clockwise (or "(+)") at 20° C. and 589 nm with the noted concentration "c" (g/100 mL) in DCM.

Preparation 18 tert-butyl 4-(acetamidocarbamoyl)piperidine-1-carboxylate

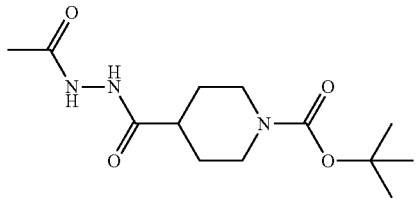 [SMILES: CC(=O)NNC(=O)C1CCN(C(=O)OC(C)(C)C)CC1]

To a flask is added 1-tert-butoxycarbonylpiperidine-4-carboxylic acid (15.0 g, 65.8 mmol) in THF (150.8 mL). The solution is stirred in an ice-water bath and 1,1'-carbonyldiimidazole (15.2 g, 92.1 mmol) is added in one portion. The reaction mixture is stirred at RT for 2 h, and acethydrazide (6.5 g, 85.5 mmol) is added in one portion at 0° C. The reaction mixture is warmed to RT and stirred overnight, and diluted with saturated aqueous NaHCO₃ solution (250 mL) and 2-methyltetrahydrofuran. The mixture is transferred to a separating funnel and the layers are separated. The aqueous layer is extracted with 2-methyltetrahydrofuran and the combined organic extracts are washed with saturated aqueous NaCl solution and dried over MgSO₄. The aqueous layer is extracted twice with DCM and the combined organic extracts are washed with saturated aqueous NaCl solution and dried over MgSO₄. The two organic solutions are combined and concentrated under reduced pressure to give a residue, which is combined with MTBE (300 mL). The mixture is stirred in a 50° C. heating block for 1 hr, stirred overnight at RT, filtered, and the filter cake is washed with MTBE. The filtered solid is dried under vacuum at 45° C. for 3 hr to obtain the title compound (14.5 g, 48.5 mmol, 73.7% yield) as a white solid. ES/MS m/z: 308 (M+Na).

Preparation 19

2-methyl-5-(4-piperidyl)-1,3,4-oxadiazole

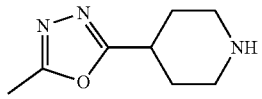

To a flask is added triphenylphosphine (16.4 g, 61.9 mmol) and DCM (177 mL). The solution is stirred at RT and 12 (16.0 g, 61.9 mmol) is added portion-wise; TEA (10.9 mL, 77.4 mmol) is added and the reaction mixture is stirred at RT for 15 min. The mixture is stirred in an ice-water bath and tert-butyl 4-(acetamidocarbamoyl)piperidine-1-carboxylate (9.3 g, 31.0 mmol) is added. The reaction mixture is stirred in an ice-water bath for 2 h, saturated aqueous NaHCO₃ solution is added, and the mixture is transferred to a separation funnel. The layers are separated and the aqueous layer is extracted with DCM. The combined organic extracts are dried over MgSO₄, filtered, and the filtrate is concentrated under reduced pressure to give a residue, which is dissolved in DCM (186 mL). To the solution is added TFA (46.5 mL) and the reaction mixture is stirred at RT overnight. The mixture is concentrated under reduced pressure and the resulting residue is combined with DCM and water. The layers are separated and the aqueous layer is extracted twice with EtOAc. The aqueous layer is basified to pH 14 with 50% aqueous NaOH solution and extracted 6 times with DCM. The combined organic extracts are washed with saturated aqueous NaCl solution, dried over MgSO₄, and concentrated under reduced pressure to give a solid, which is dried under vacuum at 40° C. for 2 h, to obtain the title compound (4.3 g, 25.9 mmol, 83% yield) as an off-white solid. ES/MS m/z: 168 (M+H).

Example 1

(−)-6-[1-[4-(5-methyl-1,3,4-oxadiazol-2-yl)-1-piperidyl]ethyl]-2,3-dihydrofuro[2,3-b]pyridine

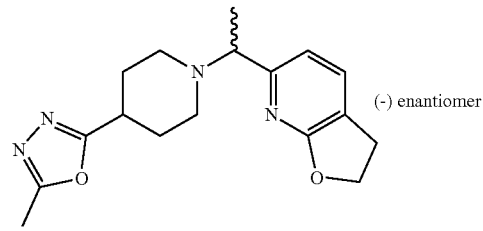 [SMILES: Cc1nnc(C2CCN(C(C)c3ccc4c(n3)OCC4)CC2)o1]

Scheme 2, step G: A mixture of (+)-6-[1-chloroethyl]-2,3-dihydrofuro[2,3-b]pyridine (247 mg, 1.3 mmol), 4-(5-methyl-1,3,4-oxadiazol-2-yl)piperidine (476 mg, 2.7 mmol) and K₂CO₃ (195 mg, 1.4 mmol) in ACN (18 mL) is irradiated at 120° C. for 150 min in a microwave. The reaction mixture is diluted with EtOAc and quenched with saturated aqueous NH₄Cl. The mixture is extracted with EtOAc and the organic phase is dried over MgSO₄. The filtrate is evaporated under reduced pressure and the resulting residue is purified by flash chromatography over silica gel, eluting with a gradient of 0-10% MeOH:DCM, to obtain a yellow oil (333 mg) after solvent evaporation of the desired chromatographic fractions. This material is pooled with additional material produced by similar methodology from additional experimental runs (total 540 mg after chromatography over silica gel) and further purified by SFC chiral chromatography (Chiral AD-H column 250×30 mm, 5 μm; column temperature 35° C.; flow rate 120 g/min), eluting with 18% IPA/0.2% DMEA in CO₂, to afford the title compound (383 mg) as an oil Analytical HPLC: $t_R$=2.35 min, >99% ee (Amyl chiral column, 3.3×150 mm, flow rate 1.5 mL/min, 18% IPA/0.2% IPAm in 82% CO₂, 35° C. column temperature, 287 nM). ES/MS m/z: 315.0 (M+H). $[\alpha]_D^{20}$=12.7 (c=0.24, MeOH). As used herein above, the terms "(−)" or "(−) enantiomer" for Example 1 refers to the enantiomer of Example 1 which has an optical rotation which is counterclockwise (or "(−)") at 20° C. and 589 nm with the noted concentration "c" (g/100 mL) in methanol.

Alternate Procedure for Example 1

Scheme 2, step H: To a stirred solution of 1-(2,3-dihydrofuro[2,3-b]pyridin-6-yl)ethanone (100 mg, 0.6 mmol)

and 2-methyl-5-(4-piperidyl)-1,3,4-oxadiazole (200 mg, 1.2 mmol) in CHCl$_3$ (5.2 mL) is added titanium(IV) isopropoxide (363 μL, 1.2 mmol) and the reaction mixture is stirred for 30 min. NaBH(OAc)$_3$ (390 mg, 1.8 mmol) is added and the reaction stirred at 40° C. overnight. The reaction mixture is diluted with EtOAc (5 mL) and saturated aqueous NaHCO$_3$ (2 mL) for 20 min, the mixture is filtered through a bed of diatomaceous earth, and the filtrate is concentrated under reduced pressure. The resulting residue is purified by reverse phase chromatography over C18 silica gel (XBridge C18, 5 μm 19×100 mm; 214 nm and 300 nm; MS-ESI 100-800), eluting with a mixture of 10 mM aqueous NH$_4$HCO$_3$, pH: ~9.0, in ACN (20% to 40% with a gradient time of 4 min), flow rate: 25 mL/min) with additional purification by SCF chiral chromatography (CHIRALPAK© AD-H column, 250×30 mm, 5 μm; column temperature 35° C.; flow rate 120 mL/min) eluting with 18% IPA/0.2% DMEA in CO$_2$, to afford the title compound (27 mg, 55% yield), after solvent evaporation of the desired chromatographic fractions. t$_R$=0.096 min, >99% ee (Amyl chiral column, 3.3×150 mm, flow rate 1.5 mL/min, 18% IPA/0.2% IPAm in 82% C02, 35° C. column temperature, 287 nM). ES/MS m/z: 315 (M+H).

Example 2

(−)-5-fluoro-6-[1-[4-(5-methyl-1,3,4-oxadiazol-2-yl)-1-piperidyl]ethyl]-2,3-dihydrofuro[2,3-b]pyridine

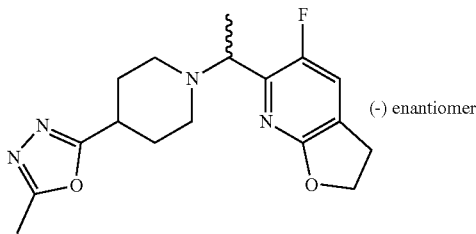 [SMILES: Cc1nnc(C2CCN(C(C)c3nc4c(cc3F)CCO4)CC2)o1]

(−) enantiomer

Scheme 3, step F: Heat a mixture of 6-(1-chloroethyl)-5-fluoro-2,3-dihydrofuro[2,3-b]pyridine (111 mg, 0.5 mmol), 4-(5-methyl-1,3,4-oxadiazol-2-yl)piperidine (107 mg, 0.6 mmol) and K$_2$CO$_3$ (85 mg, 0.6 mmol) in ACN (8 mL) at 80° C. for 27 h. Cool the reaction mixture, dilute with DCM, and quench with water. Pour the resulting biphasic mixture through a phase separator cartridge. Evaporate the DCM under reduced pressure, and purify the residue via flash chromatography over silica gel, eluting with a 50-100% gradient of EtOAc/iso-hexane, to obtain a white solid after solvent evaporation of the desired chromatographic fractions. Additionally purify by SFC chiral chromatography (CHIRALPAK© AZ-3 column 150×3 mm, 3 μm; column temp. 35° C.; flow rate 1.5 mL/min), eluting with 40% MeOH/0.2% IPA in CO$_2$, to afford the title compound in >99% ee (44 mg, 39% yield) after solvent evaporation of the desired chromatographic fractions. Analytical HPLC: t$_R$=3.7 min, >99% ee (Chiral AZ-3 column, 3.3×150 mm, flow rate 1.5 mL/min, 40% MeOH/0.2% IPAm in 60% CO$_2$, 35° C.

column temperature, 220 nM). ES/MS m/z: 333.0 (M+H). [α]$_D^{20}$=−117.5° (c=0.2, DCM).

Alternatively, a mixture (+)-6-(1-chloroethyl)-5-fluoro-2,3-dihydrofuro[2,3-b]pyridine (500 mg, 2.5 mmol), 4-(5-methyl-1,3,4-oxadiazol-2-yl)piperidine (829 mg, 5 mmol) and K$_2$CO$_3$ (1.0 g, 7.5 mmol) in ACN (25 mL) is heated to 65° C. for 72 h. The mixture is cooled, diluted with water, extracted the three times with EtOAc, and the combined organic extracts are dried over Na$_2$SO$_4$. Then extracts are filtered, and the filtrate is concentrated under reduces pressure. The resulting residue is purified by flash chromatography over silica gel, eluting with a gradient of 0.5% to 10% MeOH in DCM, to afford 586 mg of the title compound in 76.6% ee, after solvent evaporation of the desired chromatographic fractions. The title compound is further purified by SFC chiral chromatography (CHIRALPAK© AD-H, 21×250 mm, 3 μm; column temp. 40° C.; flow rate 80 mL/min), eluting with 15% MeOH/0.2% IPAm) in 85% CO$_2$, to afford the title product in 96.5% ee (457 mg, 55% yield), after solvent evaporation of the desired chromatographic fractions. ES/MS m/z: 333.0 (M+H). Analytical HPLC t$_R$=2.08 min, >96.5% ee (CHIRALPAK©AD-H, 4.6× 150 mm, flow rate 5 mL/min; 15% MeOH/0.2% IPAm in CO$_2$). [α]$_D^{20}$=−109.9° (C=0.2, DCM). As used herein above, the terms "(−)" or "(−) enantiomer" for Example 2 refers to the enantiomer of Example 2 which has an optical rotation which is counterclockwise (or "(−)") at 20° C. and 589 nm with the noted concentration "c" (g/100 mL) in DCM.

Example 3

(+)-6-[(1R)-1-[4-(5-methyl-1,3,4-oxadiazol-2-yl)-1-piperidyl]ethyl]-2,3-dihydrofuro[2,3-b]pyridine

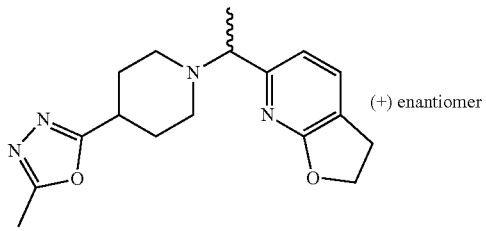 [SMILES: Cc1nnc(C2CCN(C(C)c3ccc4c(n3)OCC4)CC2)o1]

(+) enantiomer

The title compound can be prepared from (−)-6-[1-chloroethyl]-2,3-dihydrofuro[2,3-b]pyridine and 4-(5-methyl-1,3,4-oxadiazol-2-yl)piperidine, or from 1-(2,3-dihydrofuro[2,3-b]pyridin-6-yl)ethanone and 2-methyl-5-(4-piperidyl)-1,3,4-oxadiazole utilizing chiral chromatography, in a manner analogous to the procedures set forth in Example 1. [α]$_D^{20}$=+19.3° (c=0.20, MeOH)

As used herein above, the terms "(+)" or "(+) enantiomer" for Example 3 refers to the enantiomer of Example 3 which has an optical rotation which is clockwise (or "(+)") at 20° C. and 589 nm with the noted concentration "c" (g/100 mL) in MeOH.

Example 4

(+)-5-fluoro-6-[1-[4-(5-methyl-1,3,4-oxadiazol-2-yl)-1-piperidyl]ethyl]-2,3-dihydrofuro[2,3-b]pyridine

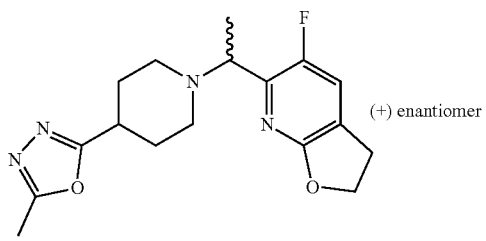 [SMILES: Cc1nnc(C2CCN(C(C)c3nc4c(cc3F)CCO4)CC2)o1]

(+) enantiomer

The title compound can be prepared from 6-(1-chloroethyl)-5-fluoro-2,3-dihydrofuro[2,3-b]pyridine and 4-(5-methyl-1,3,4-oxadiazol-2-yl)piperidine utilizing chiral chromatography in a manner analogous to the procedure set forth in Example 2. $t_R$=2.0 min under the same analytical HPLC conditions described in Example 2. $[\alpha]_D^{20}$=+107.3° (c=0.20, DCM)

As used herein above, the terms "(+)" or "(+) enantiomer" for Example 4 refers to the enantiomer of Example 4 which has an optical rotation which is clockwise (or "(+)") at 20° C. and 589 nm with the noted concentration "c" (g/100 mL) in DCM.

In Vitro Human OGA Enzyme Assay

Generation of OGA Enzyme

The nucleotide sequence encoding full-length human O-GlcNAc-β-N-acetylglucosaminidase (NM_012215) is inserted into pFastBacl (Invitrogen) vector with an N-terminal poly-histidine (HIS) tag. Baculovirus generation is carried out according to the Bac-to-Bac Baculovirus Expression system (Invitrogen) protocol. Sf9 cells are infected at $1.5 \times 10^6$ cells/mL using 10 mL of P1 virus per Liter of culture and incubated at 28° C. for 48 hrs. Cells are spun down, rinsed with PBS and the pellets stored at −80° C. The above OGA protein (His-OGA) is purified as follows: 4 L of cells are lysed in 200 mL of buffer containing 50 mM Tris, pH 8.0, 300 mM NaCl, 10% glycerol, 10 mM imidazole, 1 mM dithiothreitol (DTT), 0.1% Triton™ X-100, 4 tablets of protease inhibitors (complete EDTA-Free, Roche) for 45 min at 4° C. This cell lysate is then spun for 40 min at 16500 rpm at 4° C., and supernatant incubated with 6 mL of Ni-NTA resin (nickel-nitrilotriacetic acid) for 2 hours at 4° C.

Resin is then packed onto column and washed with 50 mM Tris, pH 8.0, 300 mM NaCl, 10% glycerol, 10 mM imidazole, 0.1% Triton™ X-100, 1 mM DTT, followed by 50 mM Tris, pH 8.0, 150 mM NaCl, 10 mM imidazole, 10% glycerol, 1 mM DTT. The proteins are eluted with 50 mM Tris, pH 8.0, 150 mM NaCl, 300 mM imidazole, 10% glycerol, 1 mM DTT. Pooled His-OGA containing fractions are concentrated to 6 ml and loaded onto Superdex75 (16/60). The protein is eluted with 50 mM Tris, pH 8.0, 150 mM NaCl, 10% glycerol, 2 mM DTT. Fractions containing His-OGA are pooled and protein concentration measured with BCA (Bradford Colorimetric Assay).

OGA Enzyme Assay

The OGA enzyme catalyses the removal of O-GlcNAc from nucleocytoplasmic proteins. To measure this activity Fluorescein di-N-acetyl-β-N-acetyl-D-glucosaminide (FD-GlcNAc, Kim, Eun Ju; Kang, Dae Ook; Love, Dona C.; Hanover, John A. Carbohydrate Research (2006), 341(8), 971-982) is used as a substrate at a final concentration of 6.7 µM (in a 384 well assay format). This fluorogenic substrate becomes fluorescent upon cleavage by OGA, so that the enzyme activity can be measured by the increase in fluorescence detected at 535 nm (excitation at 485 nm).

The assay buffer is prepared to give a final concentration of 50 mM $H_2NaPO_3$—$HNa_2PO_3$, 0.01% bovine serum albumin and 0.01% Triton™ X-100 in water, at pH 7. Compounds to be tested are diluted in pure dimethyl sulfoxide (DMSO) using ten point concentration response curves. Maximal compound concentration in the reaction mixture is 30 or 1 µM. Compounds at the appropriate concentration are pre-incubated with OGA enzyme for 30 minutes before the reaction is started by the addition of substrate. The final enzyme concentration is 3.24 nM or 0.5 nM, for the 30 or 1 µM maximal compound concentration, respectively. Reactions are allowed to proceed for 60 minutes at room temperature. Then, without stopping the reaction, fluorescence is read. $IC_{50}$ values are calculated by plotting the normalized data vs. log of the compound and fitting the data using a four parameter logistic equation.

The compounds of Examples 1 to 4 were tested essentially as described above and exhibited the following $IC_{50}$ values as set forth in Table 1:

TABLE 1

| Example | $IC_{50}$ (nM) |
| --- | --- |
| 1 | 1.24 ± 0.66 (n = 7) |
| 2 | 1.13 ± 1.02 (n = 6) |
| 3 | 611.4 (n = 1) |
| 4 | 2657 ± 606.7 (n = 2) |

These results demonstrate that the compounds of Examples 1 to 4 inhibit OGA enzyme activity in vitro.

We claim:

1. A compound of the formula:

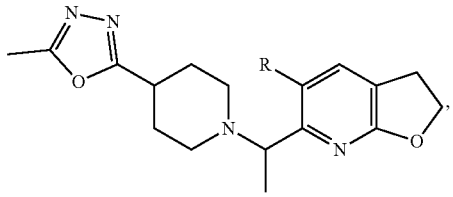

wherein R is H or F, or a pharmaceutically acceptable salt thereof.

2. The compound according to claim 1 wherein R is H, or a pharmaceutically acceptable salt thereof.

3. The compound according to claim 1 wherein R is F, or a pharmaceutically acceptable salt thereof.

4. The compound according to claim 1 wherein the compound is (−)-6-[1-[4-(5-methyl-1,3,4-oxadiazol-2-yl)-1-piperidyl]ethyl]-2,3-dihydrofuro[2,3-b]pyridine, or a pharmaceutically acceptable salt thereof.

5. The compound according to claim 1 wherein the compound is (+)-6-[1-[4-(5-methyl-1,3,4-oxadiazol-2-yl)-1-piperidyl]ethyl]-2,3-dihydrofuro[2,3-b]pyridine, or a pharmaceutically acceptable salt thereof.

6. The compound according to claim 1 wherein the compound is (−)-5-fluoro-6-[1-[4-(5-methyl-1,3,4-oxadiazol-2-yl)-1-piperidyl]ethyl]-2,3-dihydrofuro[2,3-b]pyridine, or a pharmaceutically acceptable salt thereof.

7. The compound according to claim 6 which is:
(−)-5-fluoro-6-[1-[4-(5-methyl-1,3,4-oxadiazol-2-yl)-1-piperidyl]ethyl]-2,3-dihydrofuro[2,3-b]pyridine.

8. The compound according to claim 1 wherein the compound is (+)-5-fluoro-6-[1-[4-(5-methyl-1,3,4-oxadiazol-2-yl)-1-piperidyl]ethyl]-2,3-dihydrofuro[2,3-b]pyridine, or a pharmaceutically acceptable salt thereof.

9. The compound according to claim 8 which is:
(+)-5-fluoro-6-[1-[4-(5-methyl-1,3,4-oxadiazol-2-yl)-1-piperidyl]ethyl]-2,3-dihydrofuro[2,3-b]pyridine.

10. A method of treating Alzheimer's disease in a patient, comprising administering to a patient in need of such treatment an effective amount of a compound of claim 1, or a pharmaceutically acceptable salt thereof.

11. A method of preventing the progression of mild cognitive impairment to Alzheimer's disease in a patient, comprising administering to a patient in need of such treatment an effective amount of a compound of claim 1, or a pharmaceutically acceptable salt thereof.

12. A method of treating progressive supranuclear palsy in a patient, comprising administering to a patient in need of such treatment an effective amount of a compound of claim 1, or a pharmaceutically acceptable salt thereof.

13. A pharmaceutical composition, comprising a compound or a pharmaceutically acceptable salt thereof according to claim 1 with one or more pharmaceutically acceptable carriers, diluents, or excipients.

14. A process for preparing a pharmaceutical composition, comprising admixing a compound or a pharmaceutically acceptable salt thereof according to claim 1 with one or more pharmaceutically acceptable carriers, diluents, or excipients.

* * * * *

UNITED STATES PATENT AND TRADEMARK OFFICE
CERTIFICATE OF CORRECTION

PATENT NO. : 11,214,576 B2
APPLICATION NO. : 17/053194
DATED : January 4, 2022
INVENTOR(S) : Dreyfus et al.

Page 1 of 1

It is certified that error appears in the above-identified patent and that said Letters Patent is hereby corrected as shown below:

On the Title Page

In item (56) the OTHER PUBLICATIONS:
Column 2, Line 1: Delete ""Oxadizaoles" and insert -- "Oxadiazoles --.

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*